United States Patent [19]
Shibata et al.

[11] Patent Number: 6,165,191
[45] Date of Patent: Dec. 26, 2000

[54] ULTRASONIC TREATING TOOL

[75] Inventors: Norikiyo Shibata, Yamato; Kenichi Kimura, Hachioji, both of Japan

[73] Assignee: Olympus Optical Co., Ltd., Tokyo, Japan

[21] Appl. No.: 09/318,053

[22] Filed: May 25, 1999

[30] Foreign Application Priority Data

May 28, 1998 [JP] Japan .................................. 10-147502
Oct. 29, 1998 [JP] Japan .................................. 10-308600
Jan. 18, 1999 [JP] Japan .................................. 11-009312

[51] Int. Cl.[7] .................................................. A61B 17/32
[52] U.S. Cl. ............................................ 606/169; 604/22
[58] Field of Search .................................... 606/37–40, 1, 606/169, 170, 171, 180, 174, 205–210; 601/2

[56] References Cited

U.S. PATENT DOCUMENTS

5,322,055  6/1994  Davidson et al. .
5,906,628  5/1999  Miyawaki et al. ...................... 606/169
5,980,510 11/1999  Tsonton et al. ............................ 604/22
6,063,050  5/2000  Manna et al. .............................. 604/22

*Primary Examiner*—Michael Buiz
*Assistant Examiner*—William Lewis
*Attorney, Agent, or Firm*—Frishauf, Holtz, Goodman, Langer & Chick, P.C.

[57] ABSTRACT

An ultrasonic treating tool comprises a gripping section incorporating an ultrasonic vibration element for generating an ultrasonic vibration, a vibration transmitting section for transmitting a vibration from the ultrasonic vibration element to a distal end, a clamping member opened and closed relative to the probe, and a handle provided at the gripping section to open and close the clamping member, in which a force applying point of the handle is displaced more on a proximal end side than at a swing center of the handle and the acting direction of a force application point is toward and away from the gripping section.

11 Claims, 10 Drawing Sheets

ULTRASONIC TREATING TOOL

BACKGROUND OF THE INVENTION

The present invention relates to an ultrasonic treating tool for, while grasping a living tissue portion in a body cavity of a human subject, surgically treating the living tissue portion with an ultrasonic vibration and, in particular, to an ultrasonic coagulation/cutting apparatus for performing coagulation/cutting.

For example, U.S. Pat. No. 5,322,055 discloses a surgical instrument for cutting (including a resection) and coagulating a living tissue by the use of an ultrasonic vibration. The ultrasonic surgical instrument comprises an ultrasonic probe connected to an ultrasonic vibration element, a sheath through which the probe is inserted, a blade projected from the distal end of the sheath and formed by a forward end section of the probe, and a jaw pivoted at the distal end section of the sheath and a jaw confronting the blade. By the operation of the handle provided at a proximal end side of the sheath, the jaw is swung through a rod and, while grasping a living tissue between the jaw and the blade, an ultrasonic vibration is transmitted through the ultrasonic probe to the blade and the grasped living tissue is cut or coagulated.

The operation section has a fixed handle downwardly projected at a substantially right angle to a longitudinal axis direction of the insertion section and a movable handle similarly projected downwardly. By holding the operation section while the fingers of one hand grip both the handles, the movable handle is swung. These handles are downwardly projected at a substantially right angle to the longitudinal axis direction of the insertion section and are so located as to be displaced from a center axis of the sheath section, so that the hand gripping is not stable. As a result, the swing operation of the movable handle become unstable as a whole and the living tissue grasped by the blade and jaw is liable to wobble at the distal end section of the insertion section. This tendency is aggravated under the following situation.

This type of ultrasonic coagulation/cutting apparatus is directed to principally treating a film-like living tissue, solid organ, or etc., by coagulating/cutting and it is often used to grasp a relatively great living tissue portion. When the relatively great living tissue portion is grasped, a greater swing stroke of the movable handle is involved. As a result, the movable handle is liable to wobble as a whole when the movable handle is swung and, in the distal end of the insertion section in particular, the tissue-grasped area by the blade and jaw is liable to wobble.

Further, since the fixed handle and movable operation handle are so arranged as to be projected at a substantially right angle from the longitudinal center axis of the insertion section, the hand gripping becomes unstable and need to continue firm gripping. When, in particular, operation is done over a prolonged period of time, no fatigue and numbness of the gripped hand are produced.

BRIEF SUMMARY OF THE INVENTION

The object of the present invention is to provide an ultrasonic coagulating/cutting apparatus which is excellent in operability and involves no numbness in gripped fingers/thumb of an operator during a prolonged time period of operation. The object of the present invention can be achieved by the following apparatus.

That is, there is provided an ultrasonic treating tool for surgically treating a living tissue with an ultrasonic vibration, comprising:

an ultrasonic vibration element for generating an ultrasonic vibration;

a vibration transmitting long member having a forward end section, a basic end section connected to the ultrasonic vibration element and a center axis along a length thereof from the forward end to the basic end section and transferring the ultrasonic vibration which is generated at the ultrasonic vibration element to the forward end section of the vibration transmitting long member;

an operation section for holding the ultrasonic vibration element;

a gripping section provided at the operation section and, in order to hold the operation section, having a palm-grippable configuration having a gripping center axis of the vibration transmitting long member substantially parallel to the center axis;

a probe provided at the forward end section of the vibration transmitting long member and vibrated upon receipt of the ultrasonic vibration transmitted by the vibration transmitting long member;

a clamping member moved toward and away from the probe; and an operation handle having a swing center at the operation section and swingable about the swing center to swing the clamping member, the operation handle having a thumb engaging section engaged when the gripping section is palm-gripped in which a force applying point when an operation is made with the thumb of an operator engaged on the thumb engaging section is displaced more on the gripping side than at the swing center of the handle and the direction in which the force is applied is toward a substantially center of the operation section.

According to the present invention, the gripping section is palm-gripped by the operator and stable gripping is ensured and the handle can be operated by the thumb of the palm-gripped hand on the gripping section. Therefore, the operator feels no fatigue in the gripped hand and in a time of operating the handle. Further, the gripping section and handle section can be constructed, as a compact unit, at and near the operation section, so that it is possible to obtain a simpler structure.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION (FIRST EMBODIMENT)

Figure 1:
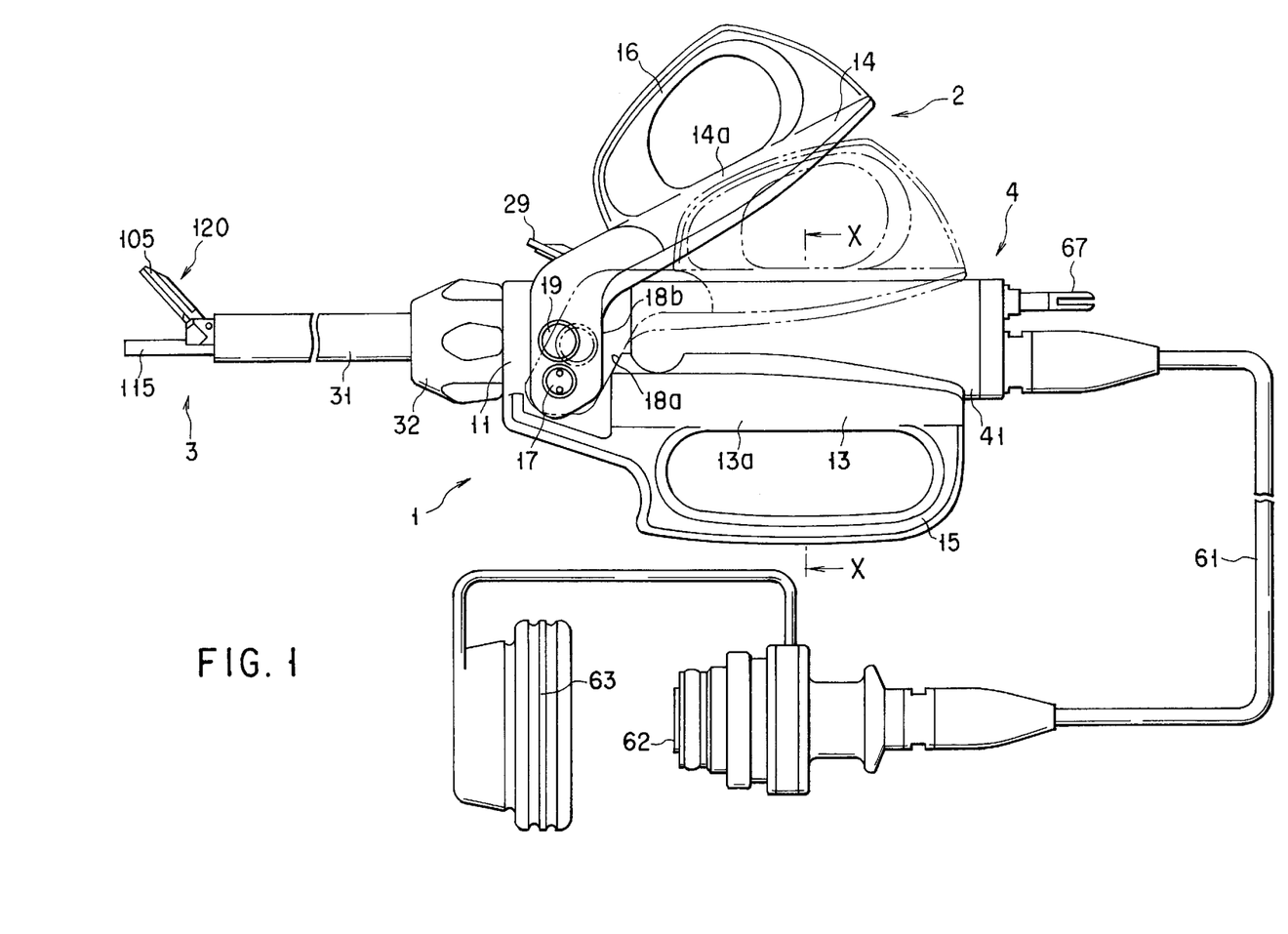
FIG. 1 is a side view showing an ultrasonic coagulating/cutting tool in an assembled state according to a first embodiment of the present invention.

An ultrasonic treating tool according to a first embodiment of the present invention will be explained below with reference to FIGS. 1 to 10. FIG. 1 shows an assembled state of a so-called ultrasonic coagulating/cutting tool as an ultrasonic treating tool. The ultrasonic coagulating/cutting tool 1 has a handle unit 2 as shown in FIG. 2A, a probe unit 3 as shown in FIG. 2B and a vibrating element unit 4 as shown in FIG. 3 and these units 2, 3 and 4 are assembled as shown in FIG. 1.

Figure 2A:
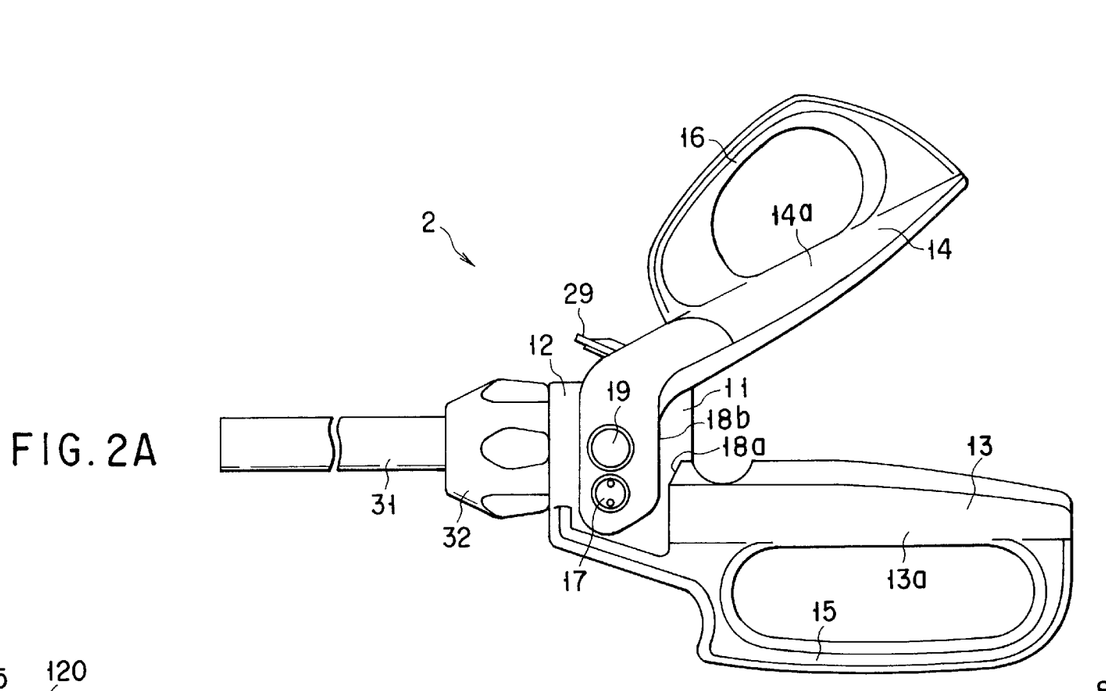
FIG. 2A is a side view showing a handle unit in the ultrasonic coagulating/cutting tool above.
Figure 2B:
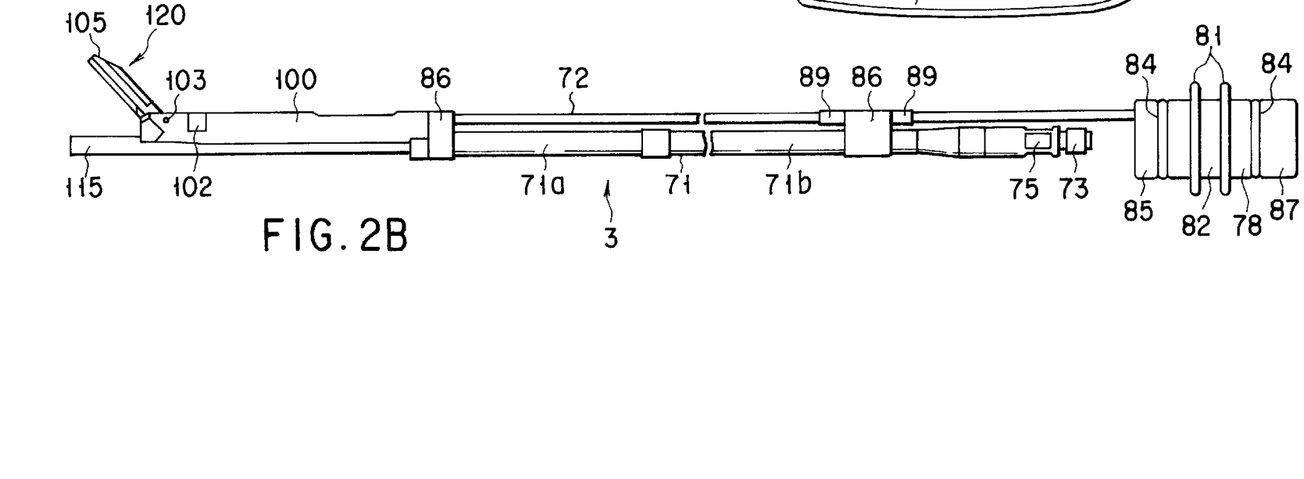
FIG. 2B is a side view showing a probe unit in the ultrasonic coagulating/cutting tool above.
Figure 3:
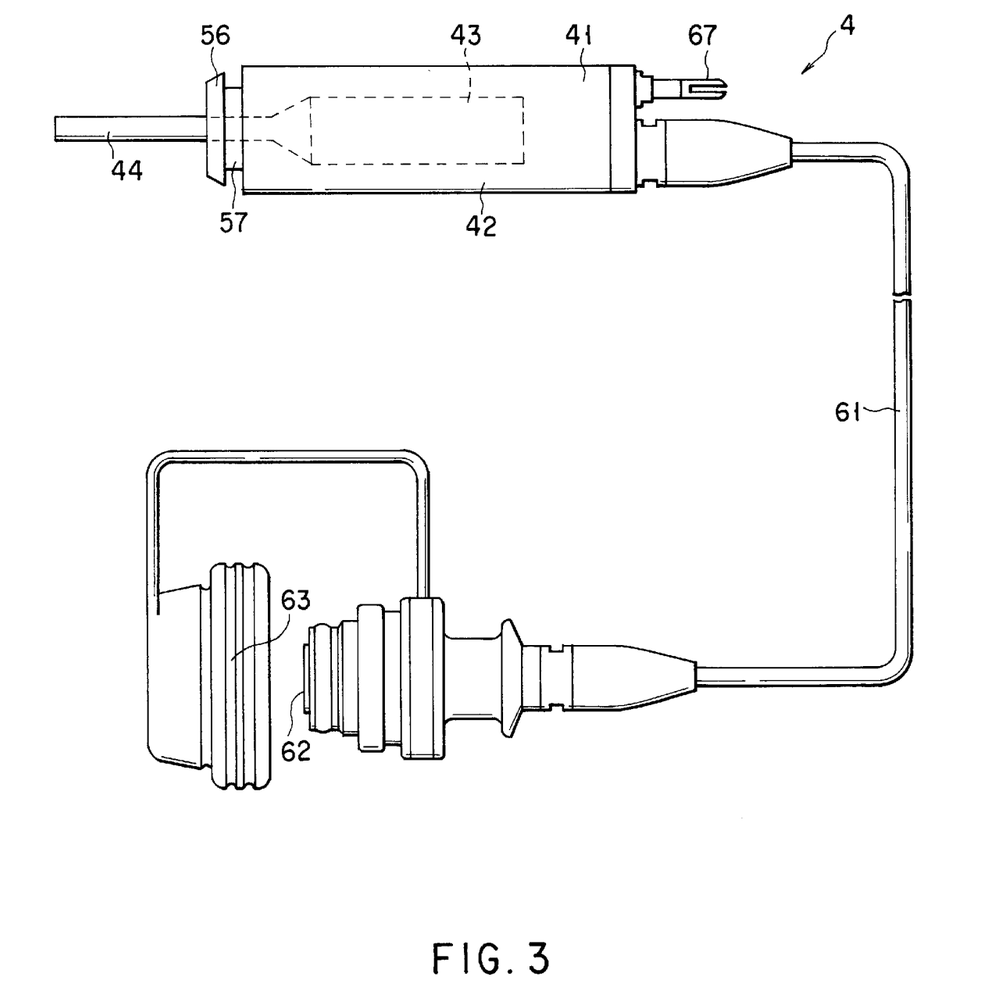
FIG. 3 is a side view showing a vibration unit in the ultrasonic coagulating/cutting tool above.

The handle unit 2 has an operation body section 12 equipped with a vibrating element connection section 11 as shown in FIG. 2A. The operation body section 12 includes a fixed, lower-side handle (grip) 13 and a swingable upper-side handle (operation handle) 14. The lower handle 13 is gripped by a hand palm as will be set out below.

The lower-side handle 13 has a finger-engaging ring 15 capable of inserting a hand's palm for finger grip. The finger-engaging ring 15 allows a plurality of fingers, other than the thumb, to be selectively inserted therein.

Figure 6:
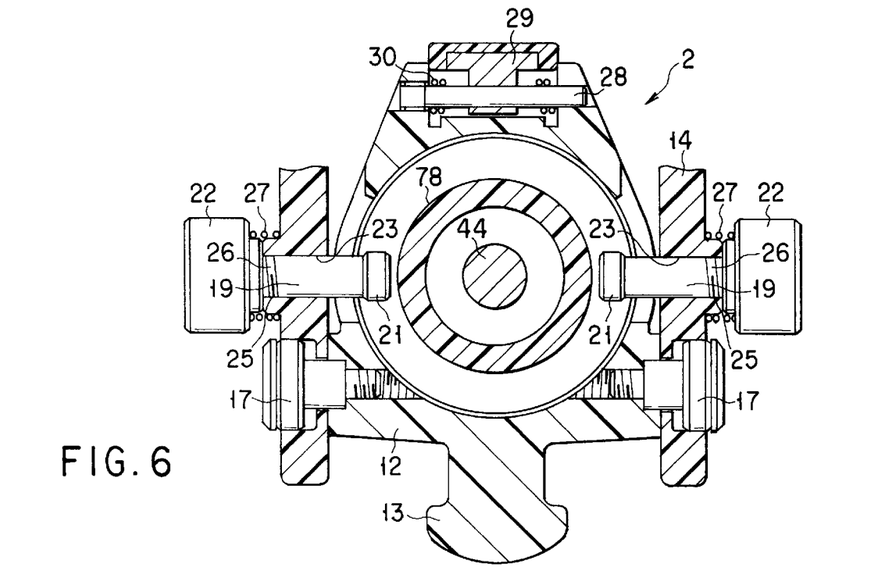
FIG. 6 is a transverse cross-section taken along line VI—VI in FIG. 5.

The upper-side handle 14 has a thumb-engaging grip (thumb grip) section 14a for hand grip through a hand's palm. A thumb-engaging ring 16 is provided at the thumb engaging section 14a. As shown in FIG. 6, the upper-side handle 14 is pivoted by shaft pins 17 threaded in the operation body section 12. The shaft pin 17 is located further ahead of the position of the grip section of the lower-side handle 13 and the position of a force applying. point of the thumb-engaging section 14a of the upper-side handle 14 is so located as to be displaced toward proximal side from a swinging center of the upper-side handle 14, that is, the grip section side, and its action direction is toward a substantially center of the operation section.

At the base portions of the upper-and lower-side handles 14 and 13 abutting sections 18b and 18a are provided which are abutted together so as to restrict their end positions when the upper-side handle 14 is swung to a closing direction.

As shown in FIG. 6, fastening screw members 19 are mounted on the base portion of the upper-side handle 14 and also serves as coupling members, that is, latching pins. The fastening screw member 19 is inserted into an associated through hole 23 at a position displaced upwardly from, or near to, the shaft pin 17 for handle swinging action. Further, engaging sections 21 are provided at the inner ends of the fastening screw members 19 and adapted to engage a probe unit 3 mounted at the operation body 12. Operation knobs 22 are formed on the fastening screw members 19 and positioned at the outer ends. The fastening screw members 19 are inserted through the through holes 23 such that they are freely movable relative to the upper-side handle 14 in their axial direction. Further, an externally threaded section 26 is so formed as to be situated on the outer end side of the fastening screw member 19 and to be inserted into the internally threaded section 25 formed in the through hole 23. The fastening screw member 19 has its intermediate section freely movable back and forth in a range situated in the through hole 23. For this reason, the engaging section 21 can be moved back to a disengaged position from a position in which the engaging section 21 is engaged with a later-described rotor and be moved forward to such an engaged position to allow the externally threaded section 26 of the fastening screw member 19 to be moved in the internally threaded section 25 to a fixed position.

Further, a coil spring 27 is set relative to the associated fastening screw member 19. The coil spring 27 acts in a way to enable the operation knob section 22 and the upper-side handle 14 to be urged away from each other. When the externally threaded section 26 is moved away from the internally threaded section 25, the fastening screw member 19 is automatically moved back from the later-described rotor side under an elastic recovery force of the coil spring 27, so that it is possible to simply effect an insertion attachment of the probe unit 3 and its withdrawal detachment.

A stopper piece 29 is mounted as a detachable member above the operation body section 12 through a swing shaft 28. The stopper piece 29 is used to fix, to a predetermined position, the vibration element unit 4 mounted on the operation body section 12. The stopper piece 29 is so urged under a coil spring 30 around the swing arm 28 as to be swung to a direction in which it is latched to the vibrating element unit 4. Normally, the stopper piece 29 is swung to a position as shown in FIG. 5.

As insertion sheath section 31 is so retained at the forward end section of the operation body section 12 as to be rotatable through the utilization of a rotation knob 32 and fixing nut 33. As shown in FIG. 5, the insertion sheath section 31 is fixedly mounted at the rotation knob 32 and the rotation knob 32 is mounted coaxial with the operation body section 12 in a way to be rotatable. A collar 34 is provided on the operation body section 12 and sandwiched between the rotation knob 32 and the fixing nut 33 so that the rotation knob 32 is so retained as to be rotatable. Here, some level of braking is applied at all times to the insertion sheath section 31 through a force of friction of the rotation knob 32 against an associated member, so that the insertion sheath section 31 is not simply to rotate.

Figure 4A:
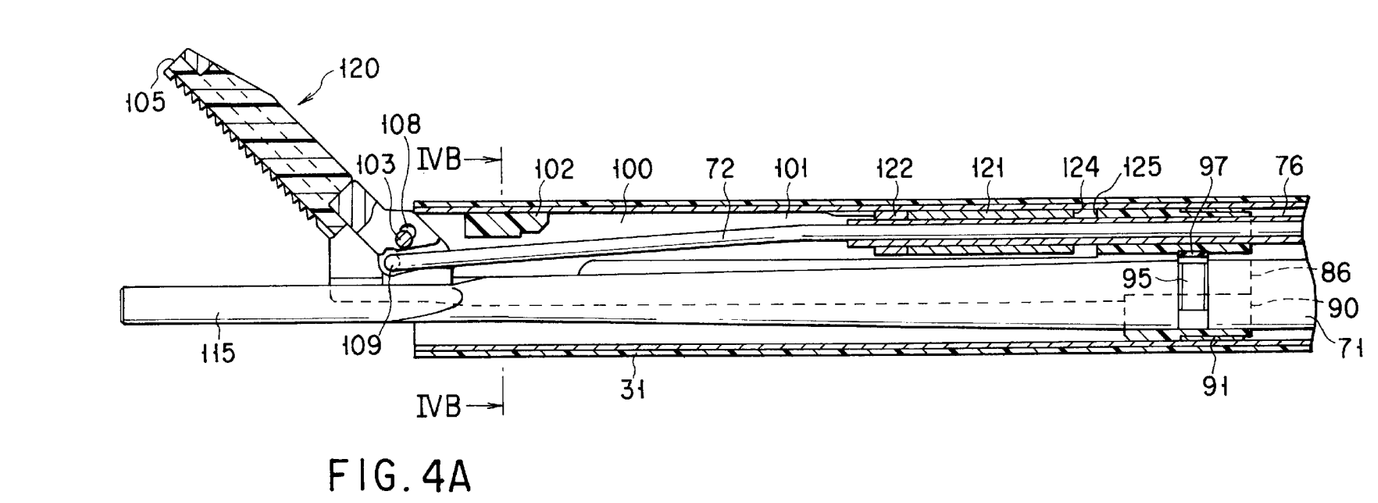
FIG. 4A is a longitudinal cross-section showing a distal end section of the ultrasonic coagulating/cutting tool.
Figure 4B:
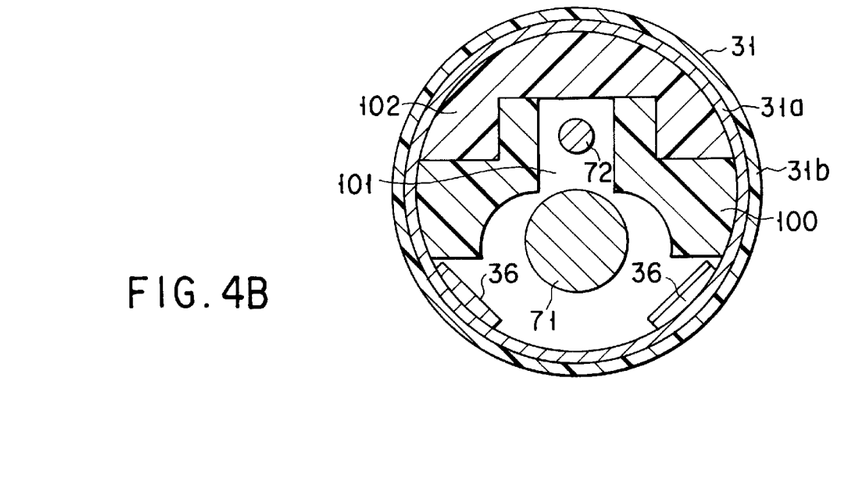
FIG. 4B is a transverse cross-section taken along line IVB—IVB in FIG. 4A.
Figure 5:
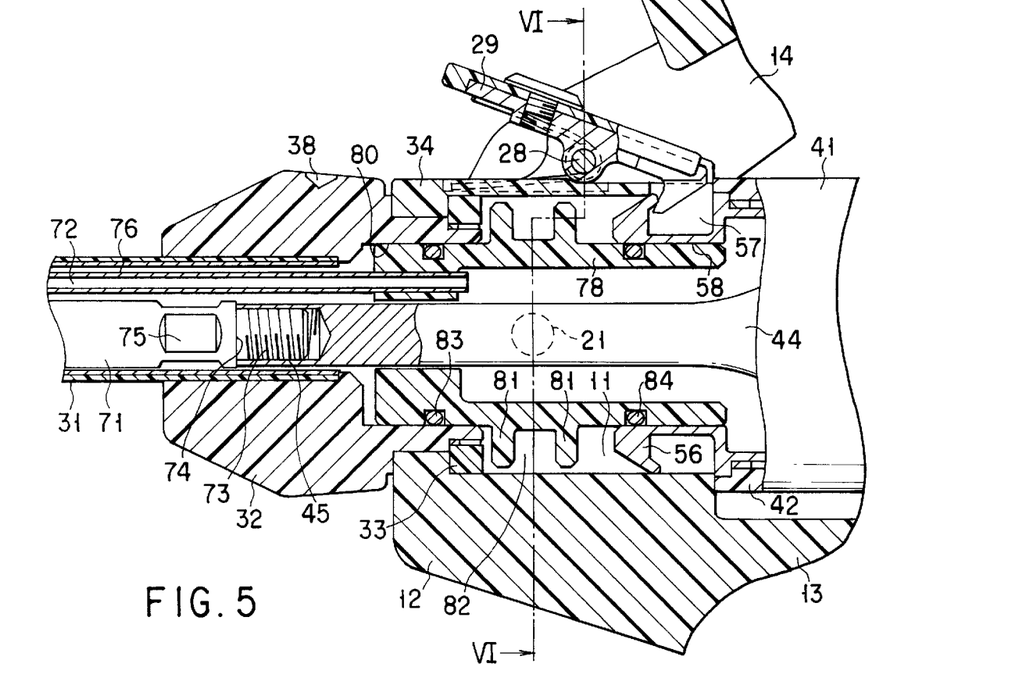
FIG. 5 is a longitudinal cross-section showing a base section of the ultrasonic coagulating/cutting tool above.

As shown in FIGS. 4A, 4B and 5, the insertion sheath section 31 is comprised of a double-tube structure comprising a core member 31a made of a rigid metal pipe and an outer covering 31b of an electrically insulating resin. Further, a pair of latching pieces 36 are provided, as shown in FIG. 4B, at a distal end section within the insertion sheath section 31. The distal end section of the probe unit 3 inserted in the insertion sheath section 31 is latched by the latching sheaths 36 to determine a rotation direction position of the probe unit 3 relative to the insertion sheath section 31. The latching piece 36 is provided by extending one portion of a distal end portion of the core member 31a and inwardly bending this extending portion. An indicator 38 is provided on the outer peripheral surface of the rotation knob 32 to indicate a latching position corresponding to the position of the latching piece 36.

As indicated in FIG. 3, the vibrating element unit 4 has the Langevin type ultrasonic vibration element 43 arranged in a cylindrical cover 42 serving also as a housing of the handpiece 41. And a horn 44 is connected to the forward end of the ultrasonic vibration element 43. As shown in FIG. 5, an internally threaded section 45 is provided at the forward end of the horn 44 to allow the rear end of the probe unit 3 to be threadably inserted.

As shown in FIG. 3, a ring-like stopper receiving member 56 is provided at the forward end portion of the cylindrical cover 42. An annular circumferential groove 57 is formed in and around the outer peripheral portion of the stopper receiving member 56. The forward end of the stopper piece 29 on the handle unit 2 side is fitted in, and latched to, the outer peripheral groove 57 of the stopper receiving member 56. The rear end portion of a rotor 78 of the probe unit 3 is fitted into an inner space 58 of the stopper receiving member 56.

As shown in FIG. 3, a long flexible handpiece cord 61 is connected to the handpiece 41 and a handpiece plug 62 is provided at the extended end of the handpiece cord 61. A water-proof cap 63 is attached to the handpiece plug 62. When the vibration element unit 4 is washed, the waterproof cap 63 covers the terminal and its neighborhood of the handpiece plug 62. A connection terminal 67 is provided at the rear end of the handpiece 41 to allow the connection of a high-frequency cord at a time of treatment with a high-frequency.

On the other hand, the probe unit 3 has a rod-like long vibration transmitting member 71 for transmitting an ultrasonic vibration and a wire-like operation drive shaft (movable member) 72 arranged there along in a substantially parallel fashion. The vibration transmitting member 71 is made of, for example, titanium material or aluminum material, which is high in sound effect and good in biocompatibility. Further, the vibration transmitting member 71 is comprised of, as shown in FIG. 2B, a forward-end side part 71a and a rear-end side part 71b, those parts being fixedly joined by screw-threading and bonding. An externally threaded section 73 is formed on the rear-end portion of the vibration transmitting member 71. The vibration transmitting member 71 is coupled to the horn 44 by inserting the portion of the externally threaded section 73 into the internally threaded section 45 formed at the forward end of the horn 44. By effecting such insertion until a stepped end face 74 of the rear end of the vibration transmitting member 71 is brought to a position where it abuts against a forward end face of the horn 44, a strong connection is achieved between the vibration transmitting member 71 and the horn 44. A wrench-turning surface 75 is formed at the outer peripheral surface of the rear end portion of the vibration transmitting member 71 so that it can be used at the attaching/detaching operation.

The operation drive shaft 72 is comprised of a wire-like member made of, for example, a stainless steel (SUS) material having a relative rigidity and spring elasticity. A thin metal pipe 76 is fitted over the operation shaft 72 such that it extends from the basic end of the operation drive shaft 72 to an intermediate portion short of a distal end side.

The rotor 78 is fixedly mounted on the rear end portion of the operation drive shaft 72. The rotor 78 is formed to a cylindrical rotor configuration with its center aligned with the center axis of the vibration transmitting member 71 in a concentric fashion. Two collars 81 are provided on the outer peripheral surface of the rotor 78 with a latching annular groove 82 defined therebetween. An engaging section 21 of the fastening screw member 19 on the upper-side handle 14, that is, the movable handle of the handle unit 2, is fitted in the engaging annular groove 82. O-rings 84, 84 are mounted one after and one before the outer peripheral surface of the rotor 78.

When the units 2, 3 and 4 are assembled together, the forward end-side outer peripheral portion 85 of the rotor 78 is fitted into a mating hole section 80 of the handle unit 2 and the rear end-side outer peripheral portion of the rotor 78 is fitted into the inner bore 58 of the stopper receiving member 56 in the inner bore of the operation body section 12. The stopper receiving piece 29 is latched to the circumferential groove 57 of the vibration element unit 4-side stopper receiving member 56. The vibration element unit 4, together with the probe unit 3, can be rotated as one unit. By the handle operation of the handle unit 2, the operation drive shaft 72 of the probe unit 3 together with the rotor 78 can be moved, in a back/forth axial direction, relative to a stationary member such as the vibration element unit 4 and vibration member 71.

As shown in FIG. 2B, the vibration transmitting member 71 and the pipe 76 fitted over the operation drive shaft 72 are mutually retained in place by a plurality of spacers 86. The respective vibration transmitting member 71 is arranged in a position corresponding to a node of the vibration involved. The spacers 86 retain the associated vibration transmitting member 71 and operation drive shaft 72 in a predetermined interval in a parallel array. Further, the respective spacers 86 except a forwardmost spacer 86 are so arranged that locating snap rings are fitted before and after each spacer on the pipe 76, that is, the pipe 76 fitted over the operation drive shaft 72, so as to inhibit the back/forth movement of the spacer 86. The respective locating snap ring 89 is fixed to the outer peripheral surface of the pipe 76 by bonding.

As shown in FIG. 4A, the forwardmost spacer 86 is situated at the node of the ultrasonic vibration nearest to a remote end of the ultrasonic probe 115 as will be set out below. The forwardmost spacer 86 may be fixed by bonding, etc., to the outer peripheral portion of the pipe 76 but, here, is loosely fitted over the outer peripheral surface of the pipe 76. The spacer 86 has a support member 90 and the locating snap ring is fitted over both the spacer 86 and support member 90 and fastened thereover or fixed by bonding as one integral unit. In assembling together these, first, the spacer 86 and support member 90 are attached to a flange 95 section of the vibration transmitting member 90 and then the locating snap ring 91 is fitted over both the spacer 86 and support member 90, followed by the bonding of both the spacer 86 and locating snap ring 91. At this time, the support member 90 is a member including the spacer 86.

As shown in FIG. 4A, the above-mentioned swing restriction flange 95 is provided on the outer peripheral portion of the vibration transmitting member 71 which is situated in the forwardmost spacer 86 position. The swing restriction flange 95 is closely fitted into an associated groove in a corresponding inner surface portion of the spacer 86 to prevent the spacer 86 from being swung around the vibration transmitting member 71. In the fitting groove of the spacer 86 a damping member 97 made up of a vibration absorbing member, such as rubber, is situated on the operation drive shaft 72 side and fitted relative to the swing restriction flange 95.

The forwardmost spacer 86 serves also as a support portion of a jaw retaining member 100 extending forwardly of this position and both the spacer 86 and jaw retaining member 100 are formed as one integral unit. The jaw retaining member 100 is supported by the spacer 86 and restricted from being moved in the axial direction of the vibration transmitting member 71 and around the axis. The jaw retaining member 100 has its forward end extended immediately before the forward end of the vibration transmitting member 71 and has a slit groove 101 from near its base end to its forward end. In the neighborhood of the forward end of the jaw retaining member 100 a reinforcing bridge 102 spans a lateral left/right portion of the slit groove 101. A jaw 105 is pivotally mounted at and near the extending forward end of the jaw retaining member 100.

In the forward end portion of the jaw retaining member 100 a pivotally support pin 103 is provided across the lateral left/right portion of the slit groove 101. The jaw 105 is mounted around the pivotally supported pin 103. The jaw 105 constitutes a so-called movable blade (movable-side grasping piece) which faces the ultrasonic probe 115 as will be set out below.

Figure 7:
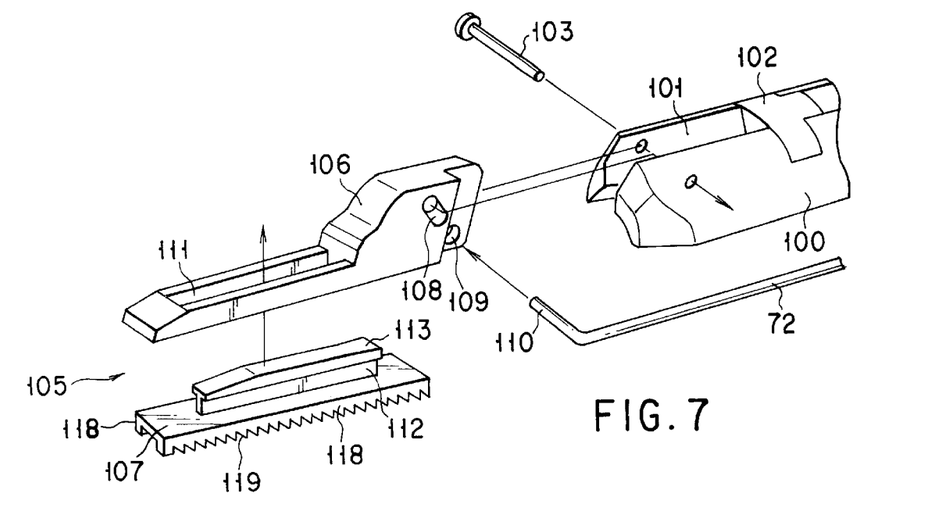
FIG. 7 is an expanded, perspective view showing a jaw section of the ultrasonic coagulating/cutting tool above.
Figure 8A:
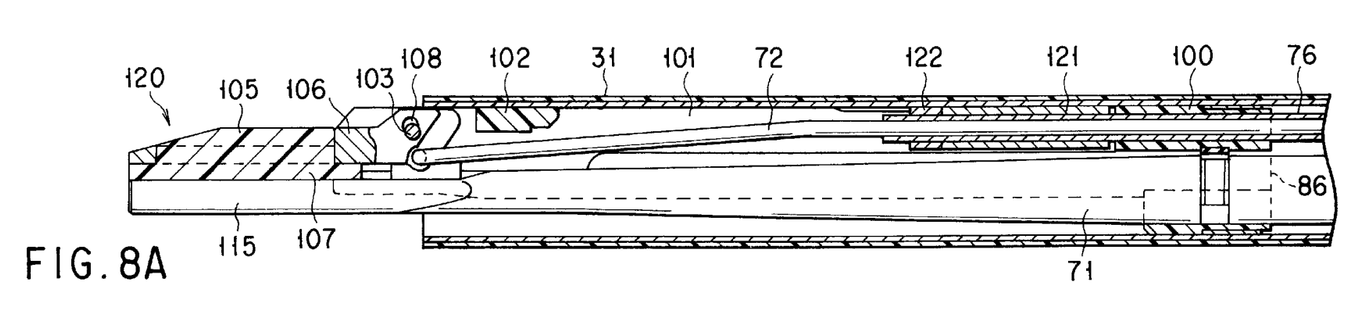
FIGS. 8A to 8C, each, are a longitudinal cross-section showing a distal end section of the ultrasonic coagulating/cutting tool above.

As shown in FIG. 7, the jaw 105 comprises a body member 106 made of metal and grasping member 107 made of a resin. A shaft support coupling hole 108 is formed near the base end of the body member 106. By inserting the pivotally support pin 103 through the coupling hole 108, the body member 106 is rotatably supported relative to the jaw retaining member 100. The coupling hole 108 for shaft support constitutes, as shown in FIG. 8A, an elongated hole diagonal relative to the axial direction of the insertion sheath section 31 and the pivotally support pin 103 is slidably inserted in the coupling hole 108. A connection hole 109 is provided in the body member 106 near and below the coupling hole 108 so as to allow the forward end of the operation drive shaft 72 to be connected. The connection hole 109 is provided across the lateral left/right section of the jaw 105. A bent section 110 of the operation drive shaft 72, that is, a bent section obtained by bending the forward end portion of the operation drive shaft 72 at a substantially right angle, is inserted into the connection section 109.

A fitting hole 111 is provided in the body member 106 as a front/back direction elongated hole. In the fitting hole 111 a corresponding projection 112 is closely fitted which is provided at the back surface of the grasping member 107. A collar 113 is provided on left and right sides at a projecting end of the projection 112.

When the projection 112 is to be fitted into the fitting hole 111, it is done so by, as shown in FIG. 7, forcibly inserting, from below, the collars 113 of the projection into the fitting hole 111 in the body member 106 while elastically deforming the collars 113 and fitting hole 111. Then through the elastic deformation, the collars 113 pass through the fitting hole 111 and closely snap-fitted in the fitting hole 111. Further, the body member 106 is sandwiched between the back surface and collars 113 of the grasping member 107 and the grasping member 107 is retained in place on the body member 106. The edges of the projection 112 and collars 113 involved when the projection 112 is fitted in the fitting hole 111 are rounded/beveled as rounded or inclined sections 116 as shown in FIG. 9 and serve as guides when the projection 112 is fitted in the fitting hole 111.

The grasping member 107 is integrally formed as a slippery resin, such as polytetrafluoroethylene. Edge portions 118 are formed at the left and right edges of grasping surfaces 117 of the grasping member 107 and the tip of the edge portion 118 is serrated to provide toothed sections 119.

The forward end portion of the vibration transmitting member 71 constitutes an ultrasonic probe (fixed-side grasping piece) 115. The portion of the ultrasonic probe 115 is so located as to face the grasping member 107 of the jaw 105. As shown in FIG. 9, the ultrasonic probe 115 is longer in vertical cross-section as shown in FIG. 9 and the outer peripheral surface portion of the ultrasonic probe 115 is sounded.

By the operable/collapsible jaw 105 swingable through the pulling/pushing of the operation drive shaft 72 and fixed ultrasonic probe 115 an ultrasonic treating section 120 is constituted by which a living tissue is grasped and coagulated/cut.

Further, a stopper mechanism is provided at a location of a jaw retaining member 100 and used to restrict a swing amount of the jaw 105 when the operation drive shaft 72 is so operated as to allow the jaw 105 to be closed. That is, as shown in FIG. 4A, a stopper tube (stopper body) 121 is fitted over an intermediate section of the operation drive shaft (movable member) 72 situated within the slit groove 101 of the jaw retaining member 100. The stopper tube 121 has its internally threaded portion provided in its inner wall surface which is mated with an externally threaded section provided on the outer peripheral surface of the pipe 76 over which the operation drive shaft 72 is fitted. By doing so, these internally and externally threaded sections are so mated as to provide a fixedly mounted unit. Since such a manufacturing/assembling means is of a screw-threaded mating type, it is possible to fine adjust the position of the stopper tube 121 in its axial direction through a manufacturing/assembling process. A tube-like nut 122 is threaded over the forward-end side of the outwardly threaded section of the pipe 76. Through the nut 122, it is possible to positively fix the stopper tube 121 by a double-nut system. A knurled section is formed, as a slippery stop section, on the outer peripheral surfaces of the stopper tube 121 and nut 122. The stopper tube 121 and nut 122, after being adjusted in these positions, are threadedly mated with, or bonded and hence positively fixed, to the outer peripheral surface of the pipe 76.

And the above-mentioned stopper mechanism is such that, when the jaw 105 is closed by pulling back the operation drive shaft 72, a rear end 124 of the stopper tube 121 is abutted against a stopper receiving face 125 comprised of a rear end face of the slit groove 101 in the jaw retaining member 100 (stationary member), so that further pull-back of the operation drive shaft 72 is inhibited and hence an operation amount of the jaw 105 is restricted. When the jaw 105 is swung, even if the grasping surface 117 of the grasping member 107 is frictionally worm through its contact with the ultrasonic probe 115, the ultrasonic probe 115 restricts an operation amount of the jaw 105 at a stage at which it is not worn deeply into contact with the body member 106.

Now an explanation will be given below about the configurations of the lower-side handle 13 and upper-side handle 14 in the above-mentioned handle unit 2. That is, as shown in FIG. 1, the lower-side handle 13 and upper-side handle 14 are situated one at an upper side and one at a lower side as viewed on an extension center axis of the insertion sheath section 31. A finger contact section (finger engaging section) 13a is formed at the lower-side handle 13 (fixed side) to provide a grip section as a palm-grippable section. The longitudinal center axis of the grip section of the lower-side handle 13 is substantially parallel to the longitudinal center axis of the vibration transmitting member 71 and insertion sheath section 31 through which the member 71 inserted.

Figure 10:
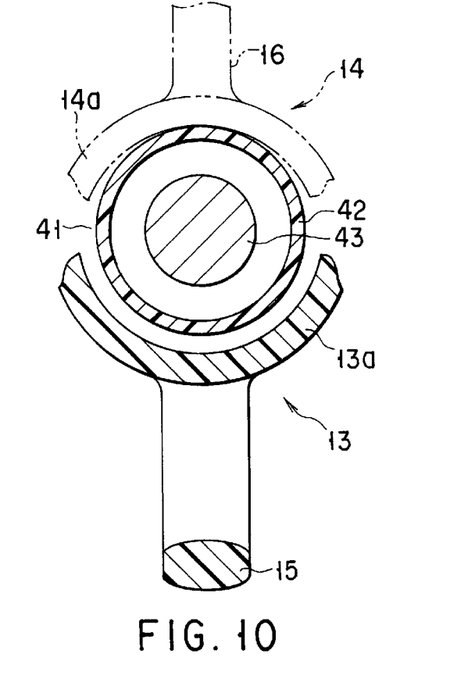
FIG. 10 is a transverse cross-section taken along line X—X in FIG. 1.

As shown in FIG. 10, the finger engaging section 13a and thumb engaging section 14a of the lower-side handle 13 and upper-side handle 14 are so formed as to be made somewhat broader than the external diameter of the cover (housing) 42 of the handpiece 41. The finger engaging section 13a and thumb engaging section 14a are so rounded as to hand-wrap the handpiece 41 portion from both above and below. The respective engaging sections 13a and 14a of the handles 13 and 14 constitute parts of a substantially cylindrical configuration around the handpiece 41. The cover area of the handpiece 41 is defined within a range of the finger engaging section 13a and thumb engaging section 14a and substantially covered with the finger engaging section 13a and thumb engaging section 14a. For this reason, during an operation, the fingers and thumb of the operator is prevented from being directly contacted with the handpiece 41 and it is possible to avoid an inadvertent rotation of the vibration element unit 4. Since the widths of the finger engaging section 13a and thumb engaging section 14a are adequately greater, the palm-gripping and finger/thumb-gripping of the handles are soft to the touch and the operator experiences any pain during a prolonged time period of use, so that he or she suffers neither fatigue nor growing pain.

Next, the ultrasonic coagulating/cutting tool 1 will be explained below. First, the ultrasonic element unit 4 is assembled on the probe unit 3 and the assembly is inserted into the handle unit 2 as shown in FIG. 1.

And the grip section of the lower-side handle 13 in the handle unit 2 is hand-gripped by the palm of one hand and the upper-side handle 14 is thumb-gripped by the thumb of the same hand. By doing so, the ultrasonic coagulating/cutting tool 1 is grasped as a whole. And the insertion sheath section 31 is guided into a body cavity by the use of a tracer, etc.

By the swing operation of the upper-side handle 14 the jaw 105 of the ultrasonic treating section 120 can be opened/closed. By swinging the jaw 105 relative to the fixed ultrasonic probe 115, a living tissue is grasped by them or, by the swing-open operation, an organ is separated or pushed aside.

In the case where the ultrasonic treatment is made with the use of the ultrasonic treating section 120, an ultrasonic vibration is applied to the ultrasonic probe 115 while grasping the living tissue of a diseased region between the ultrasonic probe 115 and the jaw 105. By doing so, the grasped living tissue is coagulated/cut.

In the process of closing the jaw 105 and sandwiching the living tissue between the jaw 105 and the ultrasonic probe 115, the ultrasonic probe 115 is elastically displaced under a pressure force from the jaw 105. That is, since the ultrasonic probe 115 is supported by the vibration transmitting member 71, the vibration transmitting member 71 is flexed at its free end portion and the ultrasonic probe 115 is displaced, while being pushed by the grasping surface 117 of the jaw 105, in a manner to follow that motion. And the living tissue is sandwiched with a proper grasping force and grasped by the jaw 105 and the ultrasonic probe 115 and coagulated/cut.

Figure 8B:
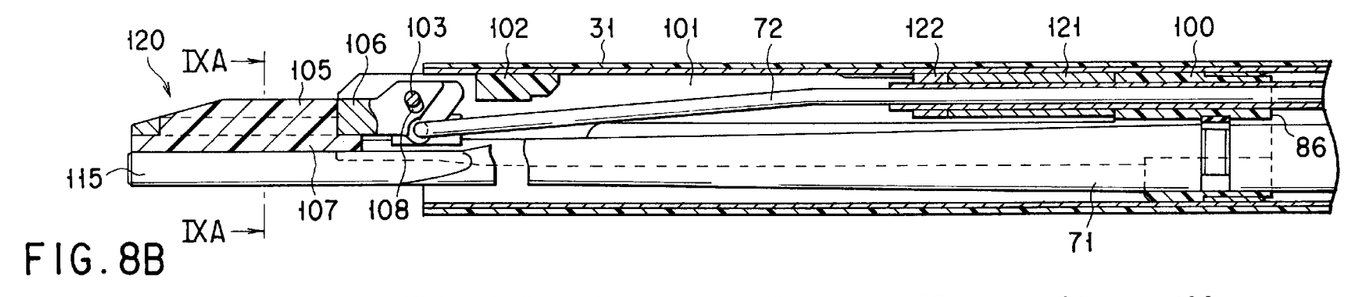
Figure 8C:
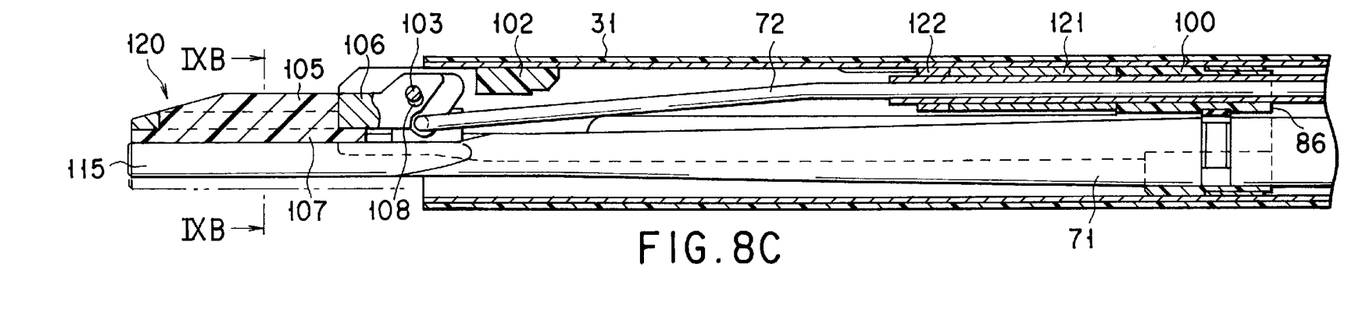

FIG. 8A shows a state in which the grasping surface 117 of the grasping member 107 of the jaw 105 is set in contact with the upper surface of the ultrasonic probe 115 and the ultrasonic probe 115 is in a not yet deformed state. FIG. 8B shows a state in which the ultrasonic probe 115 is deformed by being pushed by the jaw 105 and displaced. This is a state in which ultrasonic treatment is made with the living tissue sandwiched between the jaw 105 and the ultrasonic probe 115. When, however, the jaw 105 is swung through a given angle, then the above-mentioned stopper mechanism works and there is no further swing action and hence no excessive grasping force is applied to the ultrasonic probe 115.

Figure 9A:
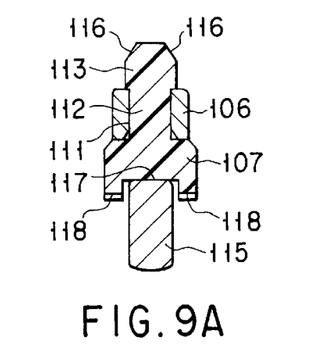
FIG. 9A is a transverse cross-section taken along line IXA—IXA in FIG. 8B.
Figure 9B:
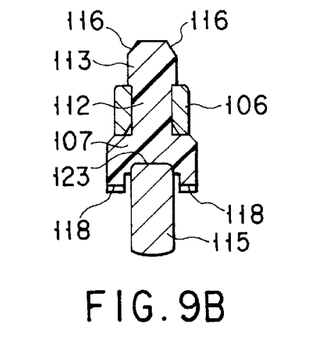
FIG. 9B is a transverse cross-section taken along line IVB—IVB in FIG. 8C.

When the living tissue portion has been cut between the jaw 105 and the ultrasonic probe 115, then the ultrasonic probe 115 while being vibrated is brought into contact with the grasping surface 117 of the grasping member 107 of the jaw 105 as shown in FIG. 9A. Each time the treatment of the living tissue is repeated, the grasping surface 117 of the grasping member 107 is worn little by little and a dent 123 is formed as shown in FIG. 9B. Before the dent 123 reaches the depth at which the body member 106 made of a metal is situated, the above-mentioned stopper mechanism works, so that the swinging motion of the jaw 105 is stopped. That is, even if the grasping surface 117 of the grasping member 107 is worn due to its contact with the ultrasonic probe 115, the operation final-end position of the jaw 105 is restricted at a stage where the dent 123 never reaches a deep position at which the ultrasonic probe 115 is contacted with the body member 106 made of a metal. For this reason, even if the grasping member 107 is worn due to its contact with the ultrasonic probe 115, the body member 106 of the jaw 105 is maintained in an area not contacted with the ultrasonic probe 115, so that this prevents the contacting of the ultrasonic probe, in a vibration state, with a metal area. The ultrasonic probe 115 in a vibration state is not contacted with the metal area, so that no damage is caused to the ultrasonic probe 115, etc., and hence there occurs no dull dissection of the living tissue. As a result, it ensures an adequately prolonged use of the ultrasonic coagulating/cutting tool and an enhanced endurance.

On the other hand, the pressing contact of the jaw 105 with the ultrasonic probe 115 is restricted by the above-mentioned stopper mechanism and an amount of grasping force is restricted within a proper range. Even if, therefore, the handles are gripped, for example, with a force as strong as practically possible or any excessive operation force is applied to the handles 13 and 14 though depending upon a difference, or extent of skill, in individual operators, it is possible to cut the living tissue, while coagulating it. Therefore, there is no risk that the living tissue such as a very small vessel in particular will be simply cut in a mechanical way. Since a predetermined grasping force is obtained at all times, there are no situations in which desired treatment is not effectively done due to no adequate heat generation resulting from the ultrasonic vibration of the ultrasonic probe 115 in the case where an excessively small grasping amount is involved or in which the ultrasonic vibration at the ultrasonic probe 115 is stopped due to an excessive grasping amount involved, As shown in FIG. 8A, the coupling hole 108 through which the pin 103 pivoted to the jaw 105 is elongated and its longitudinal direction is inclined relative to a line vertical to the grasping surface of the ultrasonic probe 115, so that the pivotally supported pin 103 is relatively movable in the coupling hole 108 in the jaw 105. For this reason, the mating of the jaw 105 with the ultrasonic probe 115 is improved and made uniform.

That is, until the living tissue begins to be grasped through the swinging motion of the jaw 105, the pivotally supported pin 103 is situated at a lower end of the coupling hole 108 in the jaw 105 as shown in FIG. 8A. When the jaw 105 is further swung with the living tissue grasped, then the jaw 105 is pulled downward, so that the pin 103 slides up to the upper end of the coupling hole 108 as shown in FIG. 8B. And the pin 103 is slidable in the coupling hole 108 in the jaw 105 and hence the grasping surfaces of both are maintained in substantially parallel grasping state, so that the mating of both can be improved. Further, it is possible to grasp more living tissue and, even if more is grasped, uniformly grasp the living tissue of interst as a whole. Since the longitudinal direction of the coupling hole 108 is inclined, a slidable action becomes smoother and the swinging motion of the jaw 105 becomes smoother.

It is to be noted that the relation of the pivotally supported pin 103 and coupling hole 108 in the jaw 105 may be formed with the pin 103 on the jaw 105 side and the coupling hole 108 on the jaw retaining member 100 side.

The stopper mechanism for restricting the swinging amount of the jaw 105 may be configured as follows. That is, it may comprise a connection member, such as a rotor 78, coupled to the rear end of the operation drive shaft 72 of the probe unit 3 and movement-operated by the handle operation on the handle unit 2 side and a fixed member confronting the rotor 78 and, when being viewed in a relative way, serving as a stationary member, in which the rear end of the rotor 78 collides against the front end of the stopper receiving member 56 to restrict the movement of the operation drive shaft 72 and, by doing so, restrict the open/close end position of the jaw 105 relative to the ultrasonic probe 115.

(SECOND EMBODIMENT)

Figure 11:
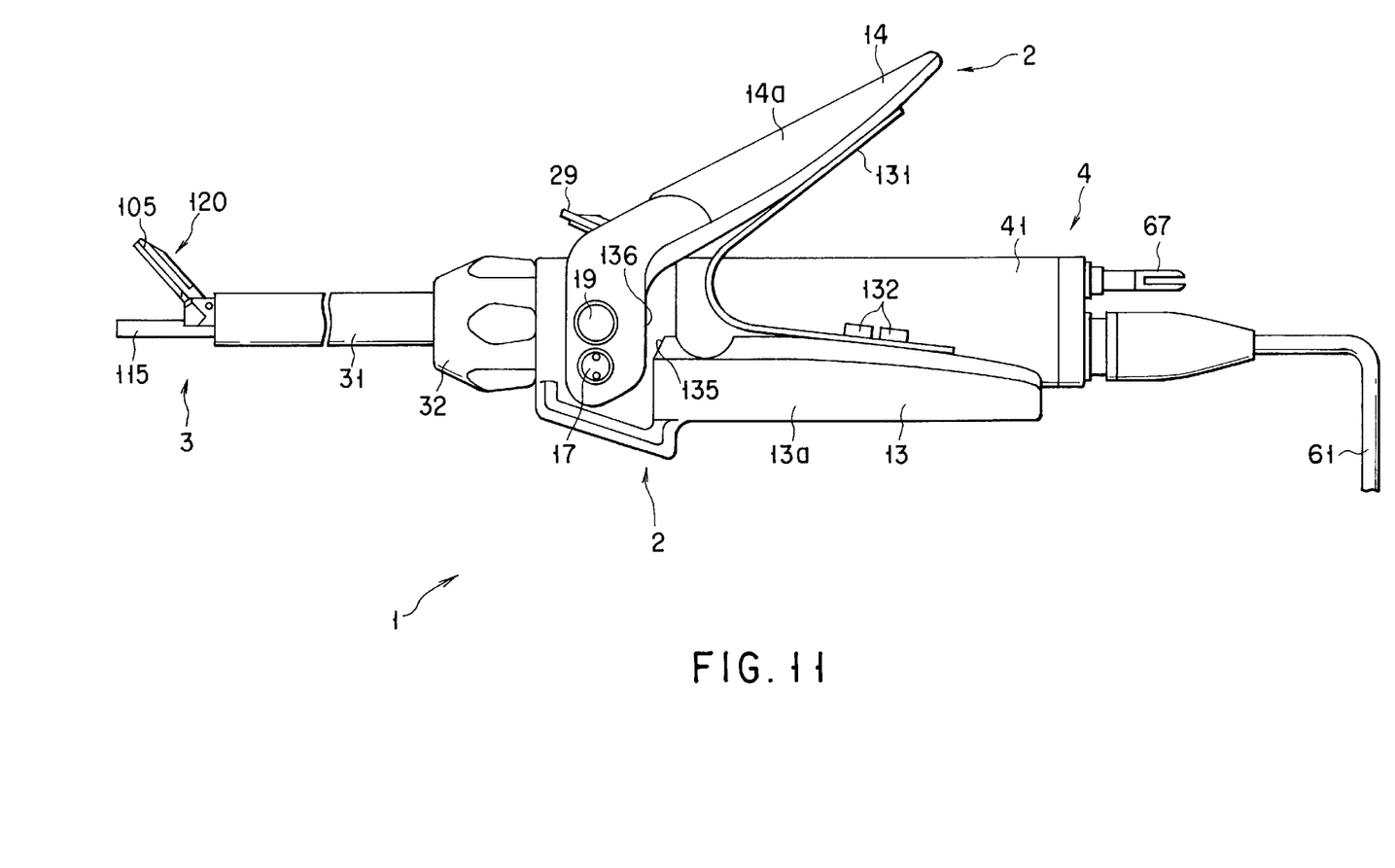
FIG. 11 is a side view showing an ultrasonic coagulating/cutting tool in an assembled state according to a second embodiment of the present invention.

A second embodiment of the present invention will be explained below based on FIG. 11. The second embodiment constitutes a variant of the handle unit 2. Here, the handle unit (variant) is such that, instead of providing the finger engaging (grip) ring and thumb engaging ring to lower-and upper-end handles 13 and 14, a spring member 131 is provided between the lower-and upper-side handles 13 and 14 to urge the respective handles 13 and 14 away from each other. The spring member 131 is comprised of a leaf spring, one end of which is mounted by a fastening means 132 to the inner surface of the lower-side handle 13 and the other end of which is joined to the inner surface of the upper-side handle 14. FIG. 11 shows a standby state in which the upper-side handle 14 is brought to an opened state under an urging force of the spring member 131. The handles 13 and 14 is urged to a normally open state and it is not necessary to provide any finger engaging rings. The other arrangement of these handles 13 and 14 is similar to the above-mentioned first embodiment.

In the second embodiment, abutting faces 135, 136 are provided on the base portions of the lower-and corresponding upper-side handles 13 and 14. These abutting faces 135 and 136 provide a stopper mechanism for restricting a swinging amount of the jaw 105. How to restrict the swinging amount of the jaw 105 is the same as that of the first embodiment.

In addition to the stopper mechanism of the first embodiment of the present invention such stopper mechanism may be provided. In the case where both the stopping mechanisms are provided, the stopper mechanism of the first embodiment acts as a main mechanism and that of the second embodiment as a subsidiary mechanism.

(THIRD EMBODIMENT)

Figure 12:
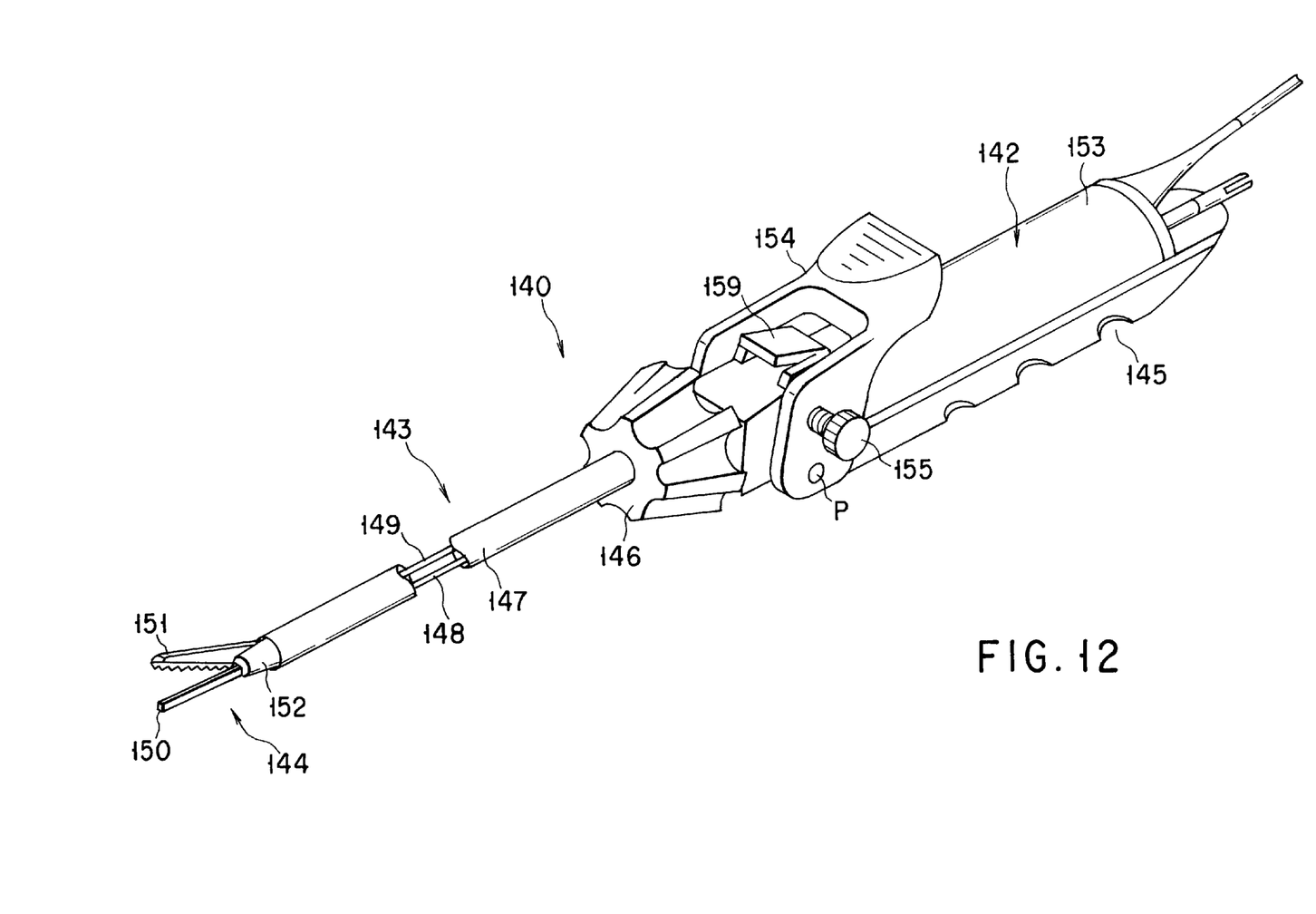
FIG. 12 is a perspective view showing a whole ultrasonic coagulating/cutting apparatus according to a third embodiment of the present invention.
Figure 13A:
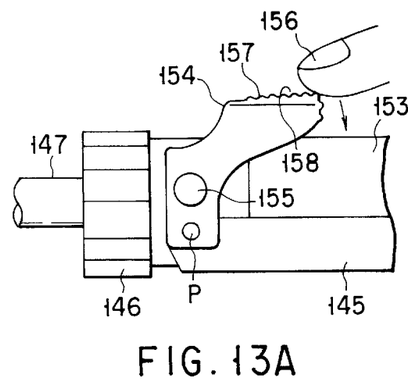
FIGS. 13A and 13B, each, are a side view for explaining the operation of a movable operation handle of the third embodiment.
Figure 13B:
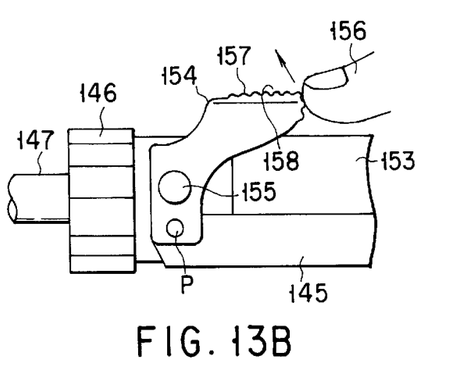

FIGS. 12 and 13 show a third embodiment of the present invention. FIG. 12 is a perspective view showing a whole structure of an ultrasonic coagulating/cutting apparatus. The ultrasonic coagulating/cutting apparatus 141 comprises an operation section 142, insertion section 143 so provided as to be connected to the operation section 142, and treating section 144 provided as a clamping section at a distal end of the insertion section 143.

A gripping section 145 is adapted to be hand-gripped by one hand's four fingers of the operator and used to hold the operation section 142. A sheath 147 is provided at the front-end side portion of the gripping section 145 and constitutes the insertion section 143 through a rotation knob 146. A vibration transmitting member 148 for transmitting an ultrasonic vibration to a distal end-side probe and an operation line 149 for operating the clamping member are inserted into the sheath 147.

A fixed edge (probe) 150 and movable edge (clamping member) 151 are provided at the distal end of the sheath 147, the fixed edge being formed by a forward end of an extension of the vibration transmitting member 148 and the movable edge being operated by the operation line. The movable blade 151 is pivoted to a jaw retaining member 152 which is fitted in the distal end portion of the sheath 147. The movable blade 151 is swung by the operation of the operation line 149 which is moved in a back/forth direction. And the movable blade is opened and closed by being moved toward and away from the fixed blade 150 which is ultrasonically vibrated. The fixed blade 150 and movable blade 151 constitute the treating section 144 serving as a clamping section for clamping a living tissue of interest.

The operation section 142 includes an ultrasonic vibration element (not shown) covered with a vibration element cover 153 of a cylindrical configuration. By doing so, an ultrasonic vibration element unit is constituted with the vibration element cover 153 as a body section. An ultrasonic vibration is generated at the ultrasonic vibration element of the ultrasonic vibration element unit and transmitted through the vibration transmitting member 148 to the fixed edge (probe) 150.

The grip section 145 is so formed as to have a lower surface portion of the vibration element cover 153 covered therewith along the vibration cover 153. The grip section 145 serves also as the fixed handle of a handle section and the finger-gripping (finger-engaging section) of the grip section 145 is formed parallel to, and along, the vibration element cover 153 of the operation section 142. The portion of the gripping section 145 is finger-gripped by one hand and the operation section 142 can be held by one hand. At this time, the body section of the operation section 142 is situated between the grip section 145 and a movable operation handle 154 and the vibration element cover (body section) 153 is located in an operator-hand's palm with which the gripping section 145 is gripped. The gripping section 145, together with a later-described movable operation handle 154, constitutes a handle unit. The handle unit is detachably mounted on the ultrasonic vibration element unit and fixed to the ultrasonic vibration element unit by the use of a stopper piece 159.

The movable operation handle 154 is swingable about a fulcrum P situated at the forward end portion of the gripping section 145 and, at a power application end portion (point) of the movable operation handle 154, the shaft portion of a latching knob 155 is rotatably mounted such that it extends through the power application end point. A latching claw (not shown) is provided at an inner end of the shaft portion of the latching knob 155. The latching claw is fitted in, and latched to, a circumferential groove in a rotor (not shown) to which the rear end of the operation rod 149 is attached. When the movable operation handle 154 is swung, the rotor is moved back and forth and the operation rod 149, which, together with the rotor, is coupled as one unit, is moved back and forth.

An externally threaded section is provided on the shaft section of the latching knob 155 such that it is mated with an internally threaded section in a through hole in the movable operation handle 154. By mating these threaded sections with each other, the latching claw is fitted in the circumferential groove in the rotor and, by doing so, can be set to a locked state.

As shown in FIGS. 13A and 13B, the surface of a thumb engaging section 158 situated at an operation force application point of the movable operation handle 154 is engaged by the thumb 156 of the operator's hand with which the gripping section 145 is gripped. A shippery-preventing ribs 157 are provided on the surface of the thumb engaging section 158. The operation force application point of the movable operation handle 154 is located more on the proximal end side than its swing center. The direction in which a force acts on the operation force application point is toward or away from the gripping section 145. That is, the force application point on which the operator's thumb 156 operates the movable operation handle 154 is located more on the gripping section 145 side of the operation section 142 than at a rotation center of the movable operation handle 154 and this structure is such that the direction in which such a force acts is toward and away from a substantially center of the body section. Further, in this embodiment, the direction in which a force applied by the thumb gripped on the movable operation handle 154 is toward or away from the gripping section 145.

The operation of the third embodiment will be explained below. First, the gripping section 145 is gripped by four fingers of one hand and, by doing so, the operation section 142 is held. The thumb engaging section 158 of the movable operation handle 154 is engaged by the thumb of the same hand. When the movable operation handle 154 is raised in a direction of an arrow in FIG. 13B, the movable operation handle 154 is swung about a swing fulcrum P and, through the operation line 149, the movable edge 151 is opened relative to the fixed edge 150.

In this way, the movable edge 151 and fixed edge 150 are set in a manner to sandwich the living tissue therebetween and, when the thumb engaging section 158 of the movable operation handle 154 is thumb-depressed in a direction as indicated by an arrow in FIG. 13A, the movable edge 151 is closed through the operation line 149.

When the ultrasonic vibration element is vibrated, it is transmitted through a vibration transmitting member 148 to the fixed edge 150 of a probe and, through the vibration of the fixed edge 150, the living tissue is coagulated/cut.

Further, when the rotation knob 146 is rotated, the sheath 147, fixed edge 150 and movable edge 151 are rotated as one unit about the center axis of the fixed edge 150 and vibration element cover 153 in a manner to follow the rotation of the rotation knob 146.

(FOURTH EMBODIMENT)

Figure 14:
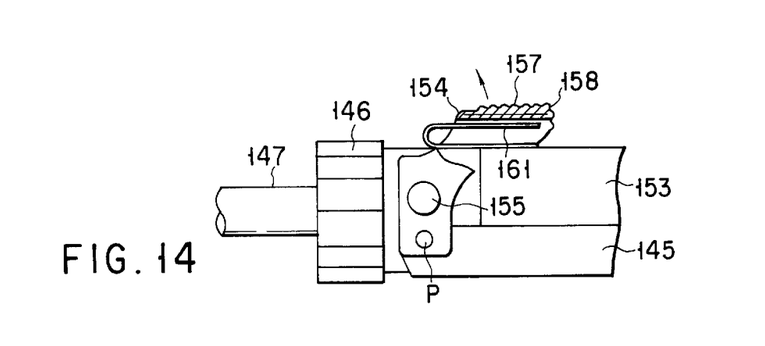
FIG. 14 is a side view showing a movable operation handle in a fourth embodiment of the present invention.

FIG. 14 shows a fourth embodiment of the present invention with similar reference numerals employed to designate similar parts or elements corresponding to those shown in the above-mentioned third embodiment and further explanation omitted.

In the fourth embodiment, inside a thumb engaging section 158 of a movable operation handle 154 an elastic body 161 is provided at a location between a vibration element cover 153 and a thumb engaging section 158 and comprised of a unshaped leaf spring. And a movable edge 151 is elastically urged by the elastic body 161 in a direction in which the movable edge 151 is opened, that is, elastically urged with the movable operation handle 154 outward.

According to the above structure, when a thumb 156 is released from a thumb engaging section 158, then the thumb engaging section 158 is moved, by an elastic force of the elastic body 161, in a direction away from the vibration element cover 153 and, in that direction, the movable operation handle 154 is swung, thus allowing the movable edge 151 to be automatically opened.

(FIFTH EMBODIMENT)

Figure 15A:
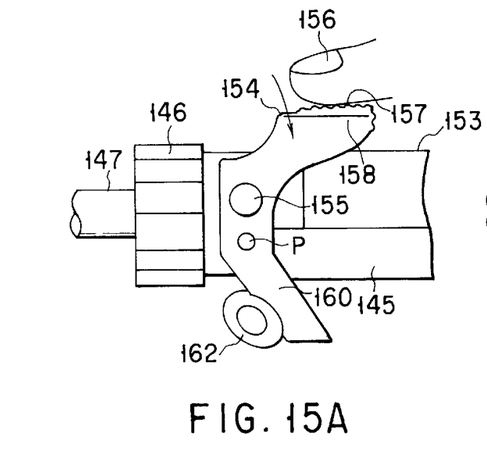
FIGS. 15A and 15B, each, is a side view for explaining the operation of the movable operation handle in the fourth embodiment above.
Figure 15B:
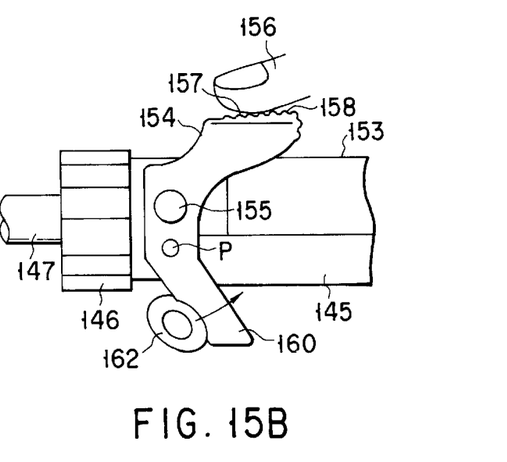

FIGS. 15A and 15B show a fifth embodiment of the present embodiment with similar reference numerals employed to designate parts or elements corresponding to those shown in the above-mentioned third embodiment and further explanation omitted.

In the fifth embodiment, a second finger engaging section 160 is provided continuous with the movable operation handle 154 in a manner to extend downward relative to the gripping section 145. The rotation radius of the second finger engaging section 160 is shorter than that of a thumb engaging section 158.

According to the above structure, a movable edge 151 is closed by depressing the first thumb engaging section 158 by an operator's thumb 156.

On the other hand, after a living tissue has been coagulated/cut, the second finger engaging section 160 is engaged by a forefinger 162 of an operator and pulled toward the operator side so that a movable edge 151 is opened.

According to the a above-mentioned third to fifth embodiments, a gripping section 145 of an ultrasonic coagulating/cutting device 141 can be palm-gripped as a whole and a fixed edge 150 and movable edge 151 at a distal end of a sheath 147 are not vibrated. And a full concentration can be paid to the operation of the movable operation handle 154, so that a delicate operation can be done at a time of coagulation/cutting. Further, the center axis of the operation section 142 corresponds to the center of finger gripping and the body section of the operation section 142 is located between the gripping section 145 and the movable operation handle 154. Therefore, the variable operation handle 154 can be operated while gripping the operation section 142 in a stabler state. As a result, an insertion section 142 is less likely to be vibrated during operation.

According to the fifth embodiment of the present invention, after coagulation/cutting has been done, the movable edge 151 is opened by pulling the forefinger 162 toward the operator. A readier operation is ensured at a time of opening the movable edge 151 and there is less fatigue on the thumb of the operator. Since the swing radius of the second finger engaging section 160 is shorter than that of the first thumb engaging section 158, the opening speed of the movable edge 151 is quickened and the quick separation of the living tissue can be done in a stable fashion. Thus, the separation of minute tissue of interest can be performed in an effective way. A tissue separation operation can be readily carried out by the repeated seasaw motion of the thumb engaging section 158 and finger engaging section 160.

Further, the thumb engaging section 158 and finger engaging section 160 are not of a ring type and there is neither fatigue nor numbness on the thumb and fingers of the operator during the operation of long duration.

Although, in the above-mentioned third through fifth embodiments, a handle unit such as the gripping section 145 and movable operation handle is constructed as separate from the ultrasonic vibration element unit, both may be assembled as an integral unit. For example, the gripping section 145 and movable operation handle 154 may be provided directly on the body section of the operation section 142.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treating tool for surgically treating a living tissue with an ultrasonic vibration, comprising:
    an ultrasonic vibration element for generating an ultrasonic vibration;
    a vibration transmitting long member having a forward end section, a basic end section connected to the ultrasonic vibration element and a center axis along a length thereof from the forward end to the basic end section and transferring the ultrasonic vibration which is generated at the ultrasonic vibration element to the forward end section of the vibration transmitting long member;
    an operation section for holding the ultrasonic vibration element;
    a gripping section provided at the operation section and, in order to hold the operation section, having a palm-grippable configuration having a gripping center axis substantially parallel to the center axis of the vibration transmitting long member;
    a probe provided at the forward end section of the vibration transmitting long member and vibrated upon receipt of the ultrasonic vibration transmitted by the vibration transmitting long member;
    a clamping member moved toward and away from the probe; and
    an operation handle having a swing center at the operation section and swingable about the swing center to swing the clamping member, the operation handle having a thumb engaging section engaged when the gripping section is palm-gripped in which a force applying point when an operation is made with the thumb of an operator engaged on the thumb engaging section is displaced more on the gripping side than at the swing center of the handle and the direction in which the force is applied is toward a substantially center of the operation section.

2. An ultrasonic treating tool according to claim 1, wherein the vibration transmitting long member, ultrasonic vibration element, probe and clamping member are rotatable as one unit.

3. An ultrasonic treating tool according to claim 1, further comprising a thumb engaging ring provided at the thumb engaging section and operable to allow the handle to be swung in mutually opposite directions, the thumb engaging ring preventing the thumb of the user from readily slipping therefrom.

4. An ultrasonic treating tool according to claim 1, further comprising a palm gripping ring provided on the gripping section to prevent the palm of the user from readily slipping therefrom.

5. An ultrasonic treating tool according to claim 1, further comprising a slip-preventing rib section provided in a thumb engaging surface range at least including the force applying point.

6. An ultrasonic treating tool according to claim 1, wherein the operation handle is formed by a seesaw type lever member with the swing center located at an intermediate section thereof and has the thumb engaging section provided on one end of the lever member and a forefinger engaging section at the palm-gripped section on the other end of the lever member.

7. An ultrasonic treating tool according to claim 6, wherein the thumb engaging section is located at one side relative to a plane including the gripping center axis of the gripping section and a forefinger engaging section at the other side relative to the plane.

8. An ultrasonic treating tool according to claim 1, further comprising an elastic body for normally urging the handle in a direction away from the gripping section where the force applying point is situated at the thumb engaging section.

9. An ultrasonic treating tool according to claim 1, wherein the gripping section is so configured as to cover a portion of the operation section, the portion of the operation section being situated in a palm-grippable position.

10. An ultrasonic treating tool according to claim 1, wherein the ultrasonic vibration element is so situated as to be incorporated at an area between the gripping section and the handle.

11. An ultrasonic treating tool according to claim 10, wherein a cover section containing the ultrasonic vibration element is surrounded with the gripping section and the handle.

* * * * *